United States Patent [19]

Whitefield

[11] Patent Number: 5,011,693

[45] Date of Patent: Apr. 30, 1991

[54] HAEMOSTATIC AGENTS

[75] Inventor: Martin Whitefield, London, England

[73] Assignee: Diomed Developments Limited, Hitchin, England

[21] Appl. No.: 425,874

[22] Filed: Oct. 24, 1989

Related U.S. Application Data

[63] Continuation-in-part of Ser. No. 264,073, Oct. 28, 1988, abandoned.

[30] Foreign Application Priority Data

Oct. 24, 1988 [GB] United Kingdom ............... 8824850

[51] Int. Cl.$^5$ .............................................. A61R 9/66
[52] U.S. Cl. ..................................... 424/455; 424/435
[58] Field of Search ............................... 424/455, 435

[56] References Cited

U.S. PATENT DOCUMENTS

| | | | |
|---|---|---|---|
| 3,856,941 | 12/1974 | Turner | 424/455 X |
| 4,073,887 | 2/1978 | McLean, Sr. | 424/467 |
| 4,224,339 | 9/1980 | van Scott et al. | 424/70 |
| 4,551,100 | 11/1985 | Fischer | 433/218 |
| 4,772,470 | 9/1988 | Inoue et al. | 424/435 |
| 4,777,041 | 11/1988 | Mercado | 424/455 X |

Primary Examiner—Thurman K. Page
Assistant Examiner—P. L. Prater
Attorney, Agent, or Firm—Stevens, Davis, Miller & Mosher

[57] ABSTRACT

Basic ferric sulphate or hydrated aluminum chloride solution used as a haemostatic agent, is made easier to handle and apply by gelling with colloidal silicon dioxide.

12 Claims, No Drawings

HAEMOSTATIC AGENTS

This application is a continuation-in-part of application Ser. No. 264,073, filed Oct. 28, 1988, now abandoned.

This invention relates to haemostatic agents and their preparation and use.

An aqueous solution containing about 20 to 22% w/v calculated as iron (III) of ferric subsulphate (or basic ferric sulphate of suggested formula $Fe_4O(SO_4)_5$ or $Fe_4(OH)_2(SO_4)_5$) is widely used as a haemostatic agent under the name of Monsel's solution. The concentration is calculated in terms of iron (III) owing to the uncertainty about the precise formula of the Monsel salt. The solution is applied by topical application to superficial wounds and abrasions and has proved particularly useful after punch biopsies and removal of localised skin lesions by curettage. It has also been proposed as a haemostatic agent for use after cervical biopsy, shave excision, nail fold biopsy, nail matricectomy, and cerumen removal.

While Monsel's solution is an effective haemostatic agent, it is not entirely satisfactory in use. More particularly, it is a very acid solution and, because of its iron content, is liable to cause staining which creates serious problems if it is spilled. It must therefore be handled and applied with care. Additionally, because of its high concentration which approaches saturation, the solute is liable to crystallise out even on short term storage and especially if the solution is stored at low temperatures or allowed to evaporate.

Solutions of aluminium chloride hexahydrate in water or aqueous alcohol (ethanol or isopropyl alcohol) containing 20 to 70% w/v of the salt (calculated as the hydrated salt) are also used as haemostatic agents.

We have now discovered that these known haemostatic solutions may be made very much easier and more convenient to handle without in any way impairing their valuable haemostatic properties, by formulating them as gels containing colloidal silicon dioxide.

The present invention accordingly provides a haemostatic composition in the form of an aqueous or aqueous alcoholic solution of basic ferric sulphate or aluminium chloride hexahydrate, and sufficient colloidal silicon dioxide to gel the mixture. The solution is gelled when it cannot be poured but can still be expelled from a narrow nozzle and applied in small quantity to the site to be treated. The gel is thixotropic and its viscosity is reduced markedly when it is subjected to shear. This makes measurement of the viscosity unreliable, but it is in practice satisfactory to rely on visual inspection to obtain a gel which is sufficiently mobile for transfer and packing in nozzled, unit dose containers. Unexpectedly, in the presence of the silicon dioxide, the gel shows a greatly reduced tendency to crystallise even on prolonged standing at reduced temperatures and shows a reduced tendency to dry out.

Colloidal silicon dioxide is submicroscopic fumed silica prepared by the vapour phase hydrolysis of a silicon compound. It is commercially available in a variety of particle sizes (and surface areas). For use in the present invention colloidal silicon dioxide preferably has a surface area in the range of 150 to 250 $m^2/g$ by BET measurement and especially about 200 $m^2/g$. Only a small proportion, usually in the range of 3 to 6%, preferably 4 to 5%, by weight of the colloidal silicon dioxide is required to produce a gel when incorporated into Monsel's solution. A slightly higher amount, 4 to 10% by weight, is required to gel aluminium chloride solution.

Surprisingly it has been discovered that the Monsel's solution must have a sufficient content of sulphate for the required gel to be produced with a small quantity (below 6%) of colloidal silicon dioxide. Some samples of Monsel's solution contain insufficient sulphate to produce a gel with this quantity of colloidal silicon dioxide, and in that case it is necessary to add a small amount (up to 10% weight for weight) of concentrated sulphuric acid to gel the mixture. The specific gravity of Monsel's solution provides a convenient indication of its sulphate content. A density of >1.6 normally indicates that no additional sulphuric acid is required.

Under normal circumstances, silicon dioxide gels aqueous solutions only between pH limits of 5 and 9. Since the pH of Monsel's solution is below 0.5, it is very surprising that the gelling effect actually occurs. This may be due to a contribution from the sulphate ion as, if there is insufficient sulphate present in the basic salt to produce a gel, further sulphuric acid must be added as noted above. Addition of other acids, such as hydrochloric acid, is far less effective.

Monsel's solution may be prepared in known manner. For use in the present invention it should have a pH below 0.5 and for rapid haemostatic activity, a concentration of iron (III) in the range 15 to 20% w/v, corresponding approximately to a Monsel's salt content in the aqueous solution of 48 to 64% w/v, not including the added colloidal silicon dioxide. Lower concentrations may be used where a slower effect is acceptable, i.e. 6 to 15% w/v iron (III), corresponding approximately to 20 to 48% w/v of Monsel's salt, although this would require a higher concentration of silicon dioxide, (e.g. up to 10%), to produce a suitable gel. Concentrations of iron (III) above 20% w/v up to saturation can also be used but such solutions are liable to deposit crystals on long standing even in the presence of the colloidal silicon dioxide, and such concentrations are therefore not preferred when the ability to withstand long storage, e.g. up to 2 years, without crystallization is required.

Aluminium chloride hexahydrate solutions in concentrations between 20 and 70% in aqueous alcoholic (ethanol or isopropyl alcohol) medium may be gelled using the same grade of colloidal silica (4–10% by weight) with the addition if necessary of hydrochloric acid (0.5–5% weight for weight).

The gelling agents normally used in compositions for topical application are unsuitable for use with these solutions because of the high degree of acidity of the latter which decomposes gelling agents such as cellulose derivatives or gums, or is incompatible with gel formation by other agents (e.g. Carbopol). Further the high concentration of iron (III) in Monsel's solution is incompatible with gel formation with materials such as agar or silicate salts which would react with the basic ferric sulphate. Surprisingly it has been found that colloidal silicon dioxide can be used to produce a semi-solid gel from either Monsel's solution or aluminium chloride solution which is clear, or at least translucent. The gel is easy to apply topically and shows a greatly reduced tendency to spread from the desired application area or to crystallise out on storage, as compared with the ungelled solutions while the presence of the silicon dioxide in no way interferes with the haemostatic activity. Surprisingly, it actually appears to enhance the effect and to encourage faster blood coagulation.

The gelled solution is conveniently dispensed in small plastic containers each containing a unit dosage of the gel, i.e. enough for one haemostatic application. The individual plastic containers must, of course, be resistant to the gel and are preferably squeezable to extrude the gel. Small sachets of, for example, polyethylene or other inert plastics material are suitable. Dispensing the gel from such containers is a very much simpler more rapid and more certain procedure than applying ungelled Monsel's solution or ungelled aluminium chloride solution. Moreover, the risk of spillage, which can be very inconvenient with such highly acid materials is avoided.

The following Examples illustrate the invention.

EXAMPLE 1

1. Preparation of Monsel's solution

Sulphuric acid (55 ml) is added to distilled water (800 ml) in a suitable vessel and the mixture is heated to about 100 C. Nitric acid (75 ml) is then added. Hydrated ferrous sulphate (1045 g) in coarse powder form is then added in four approximately equal portions one after the other with stirring after each addition until the effervescence ceases. If, after all the ferrous sulphate has been added the solution is black, nitric is added a few drops at a time with heating and stirring until the black colour has disappeared and red fumes are no longer evolved. The solution is then boiled until it assumes a red colour and free nitrate can no longer be detected in it. The volume of the mixture is made up to about 1000 ml by addition of distilled water as needed. Finally the solution is cooled, adjusted in volume if necessary to 1000 ml, and, if necessary, filtered to remove any suspended solid. The resulting solution is assayed for iron (III) and the weight per ml is determined. The solution is then diluted, if necessary, using water and/or sulphuric acid to obtain the required strength and sulphate content necessary for formulating into the gel. A solution containing for example 15 to 20 g of iron (III) per 100 ml may be used for the next step.

2. Preparation of the gel

Colloidal silicon dioxide having a surface area by BET measurement of $200 \pm 30$ m$^2$/g (Wacker-Chemie Hydrophilic HDK grade N 20) is added to the Monsel's solution prepared as described above at a concentration of 4.5% by weight and thoroughly mixed in to produce a homogeneous dispersion. The mixture is left for 2 to 3 hours for the particles of silica to become fully hydrated and then mixed further to disperse any gel agglomerates and provide a smooth homogeneous preparation. At this stage, if the viscosity is too low and the solution has not gelled, concentrated sulphuric acid is added in small portions with continuous mixing until the required viscosity is obtained. This is indicated by the formation of a semi-solid aqueous gel which may be packed conveniently into a unit dose, polyethylene, tube-like container and dispensed by squeezing through a narrow orifice (1-3 mm diameter) onto or into the affected skin site. Measuring the actual viscosity is only of theoretical interest as this type of gel is highly thixotropic which is an advantage in clinical usage. Although under shear the gel loses viscosity and may therefore easily be extruded from its container and applied to the site, once deposited on or in the tissues it rapidly regains it original viscosity and recovers its relative immobility. This avoids the problems caused by spreading which occur with Monsel's solution.

EXAMPLE 2

1. Preparation of aluminium chloride solution

Aluminium chloride hexahydrate (500 g) is dissolved in distilled water, with warming and then cooling if necessary, to produce a final volume of 1000 ml.

2. Preparation of the gel

The aluminium chloride gel is prepared in exactly the same manner as described in Example 1 for Monsel's solution with the exception that the gelling agent is added at a concentration of 6.5% by weight of the solution and concentrated hydrochloric acid is added, as necessary, to produce the required viscosity.

I claim:

1. A gel for topical application as a hemostatic agent consisting essentially of a solution in water of basic ferric sulphate at a concentration within the range 6 to 20% w/v Fe(III) and sufficient for hemostatic activity, the said solution having a containing sufficient sulphate and colloidal silicon dioxide to gel the solution.

2. A gel for topical application as a hemostatic agent consisting essentially of an aqueous alcoholic solution of hydrated aluminium chloride at a concentration sufficient for hemostatic activity, said concentration being 20 to 70% w/v of said hydrated aluminium chloride, calculated on the hydrated salt, and 4 to 10% by weight of said gel of colloidal silicon dioxide to gel the solution.

3. A gel according to claim 1 comprising 15 to 20% w/v of basic ferric sulphate, calculated as iron (III).

4. A gel according to claim 3 in which the proportion of the colloidal silicon dioxide is 3 to 6% by weight.

5. A gel according to claim 4 in which the proportion of colloidal silicon dioxide is 4 to 5% by weight.

6. A gel according to claim 2 comprising 20 to 70% w/v of hydrated aluminium chloride (calculated as the hydrated salt) and in which the proportion of the colloidal silicon dioxide is 4 to 10% by weight.

7. A gel according claim 1 which the colloidal silicon dioxide has a surface area by BET measurement of 150 to 250 m$^2$/g.

8. A gel according to claim 2 in which the colloidal silicon dioxide has a surface area by BET measurement of 150 to 250 m$^2$/g.

9. A gel according to claim 1 having a pH of about 0.5 or less.

10. A plastic sachet containing a unit dose of a gel as claimed in claim 1.

11. A plastic sachet containing a unit dose of a gel as claimed in claim 1.

12. A plastic sachet containing a unit dose of a gel as claimed in claim 2.

* * * * *